(12) United States Patent
Simmons

(10) Patent No.: US 9,775,789 B2
(45) Date of Patent: Oct. 3, 2017

(54) TOPICAL LIPOSOME COMPOSITIONS CONTAINING PHENOLIC ANTI-INFLAMMATORY AGENTS AND THEIR METHODS OF PREPARATION

(71) Applicant: D& J ROSEE INC., Brossard, Quebec (CA)

(72) Inventor: Donald L. Simmons, Dollard des Ormeaux (CA)

(73) Assignee: D & J Rosée Inc., Brossard (CA)

( * ) Notice: Subject to any disclaimer, the term of this patent is extended or adjusted under 35 U.S.C. 154(b) by 93 days.

(21) Appl. No.: 14/648,818

(22) PCT Filed: Dec. 6, 2013

(86) PCT No.: PCT/CA2013/001013
§ 371 (c)(1),
(2) Date: Jun. 1, 2015

(87) PCT Pub. No.: WO2014/085914
PCT Pub. Date: Jun. 12, 2014

(65) Prior Publication Data
US 2015/0342843 A1    Dec. 3, 2015

Related U.S. Application Data

(60) Provisional application No. 61/734,111, filed on Dec. 6, 2012.

(51) Int. Cl.
| A61K 8/14 | (2006.01) |
| A61K 8/97 | (2017.01) |
| A61K 8/55 | (2006.01) |
| A61K 8/63 | (2006.01) |
| A61Q 19/00 | (2006.01) |
| A61K 36/82 | (2006.01) |
| A61K 9/127 | (2006.01) |
| A61K 31/353 | (2006.01) |
| A61K 8/49 | (2006.01) |
| A61K 9/00 | (2006.01) |

(52) U.S. Cl.
CPC .............. *A61K 8/14* (2013.01); *A61K 8/498* (2013.01); *A61K 8/55* (2013.01); *A61K 8/63* (2013.01); *A61K 8/97* (2013.01); *A61K 9/0014* (2013.01); *A61K 9/127* (2013.01); *A61K 31/353* (2013.01); *A61K 36/82* (2013.01); *A61Q 19/00* (2013.01); *A61Q 19/007* (2013.01); *A61K 2800/10* (2013.01)

(58) Field of Classification Search
CPC ...................................................... A61K 8/14
See application file for complete search history.

(56) References Cited

U.S. PATENT DOCUMENTS 4,877,561 A * 10/1989 Iga .................. A61K 9/1277
                                                              264/4.3
5,653,998 A * 8/1997 Hamann ............ A61K 9/0019
                                                              424/450

* cited by examiner

*Primary Examiner* — Benjamin Packard
(74) *Attorney, Agent, or Firm* — Damien Calvet; Brouillette Legal Inc.

(57) ABSTRACT

Liposomal topical compositions containing phenolic anti-inflammatory agents, and methods for making thereof, are presented. These compositions are generally used for helping to prevent solar radiation-induced skin damage and helping to prevent and/or treat inflammatory dry skin conditions caused by eczema and contact dermatitis.

22 Claims, No Drawings

TOPICAL LIPOSOME COMPOSITIONS CONTAINING PHENOLIC ANTI-INFLAMMATORY AGENTS AND THEIR METHODS OF PREPARATION

CROSS-REFERENCE TO RELATED APPLICATIONS

The present patent application claims the benefits of priority of U.S. Provisional Patent Application No. 61/734,111, entitled "Topical Liposome Compositions Containing Phenolic Anti-Inflammatory Agents and Their Methods of Preparation", and filed at the United States Patent and Trademark Office on Dec. 6, 2012, the content of which is incorporated herein by reference.

FIELD OF THE INVENTION

This invention relates to topical compositions containing phenolic anti-inflammatory agents partially encapsulated within multilamellar vesicles, and methods for making thereof. The invention also relates to the uses of such topical compositions to help prevent solar radiation-induced skin damage and to help prevent and/or treat reddened itchy dry skin conditions due to inflammatory dermatoses such as eczema and contact dermatitis.

BACKGROUND OF THE INVENTION

Phenols are defined as organic compounds possessing one common structural feature—one or more aromatic rings having a minimum of one hydroxyl substituent per ring. The smallest phenol chemically is p-hydroxy benzene once widely used as an antiseptic but still available in some retail stores as a mildly disinfectant soap. Svobodova et al (Biomed Papers, 2003 147(2):137-145) have published an excellent review of natural phenols, phenolic acids and flavonoids derived from plants and the role they play in the prevention of UV-induced skin damage in humans. One plant-derived phenol currently undergoing extensive testing in the medical arena is trans-resveratrol or trihydroxy stilbene isolated from red grapes. Naturally occurring phenolic acids contain two distinguishing features: the hydroxycinnamic and hydroxybenzoic acid groups. Typical examples are caffeic and ferulic acids which have been proven effective in protecting human skin from UVB-induced erythema. Flavonoids are polyphenolic compounds that are ubiquitous in nature and are categorized, according to chemical structure into flavonols, flavones, flavanones, isoflavones, catechins, anthocyanidins and chalcones. Over 4,000 flavonoids have been identified and have aroused considerable interest recently because of their potential beneficial effects on human health such as antiviral, anti-allergic, anti-platelet, anti-inflammatory, antipruritic, anti-microbial, anti-tumor and antioxidant activities. One natural polyphenol that has been extensively tested in both animals and humans is a catechin from green tea leaves called epigallocatechin gallate (EGCG) which is used as an example for this disclosure.
Epigallocatechin Gallate and Solar Radiation:

The many benefits of topical application of green tea and its catechin components are summarized in a June 2005 issue of Life Extension Magazine entitled "Why sunscreens do not fully prevent skin cancer" (www.lef.org/magazine/magazine). The summary cites scientific articles showing that EGCG provides broad-spectrum protection by preventing several pathological changes associated with sun damage: inflammation, oxidative stress, DNA damage and immune system deficits. In one such article, Katiyar et al (Carcinogenesis, 2001 22(2):287-294) investigated the effects of topical application of EGCG to human skin on UV-induced markers of oxidative stress. Using immunochemistry on punch biopsies, the authors found that application of EGCG before a single UV exposure (4× minimal erythema dose or MED) markedly decreased UV-induced production of hydrogen peroxide, nitric oxide and lipid peroxide in both epidermis and dermis. EGCG pretreatment also inhibited UV-induced infiltration of inflammatory leukocytes into the skin. Leukocytes are considered to be the major producers of reactive oxygen species (ROS) which can cause a depletion of immune system cells. The in vitro ROS scavenging activity of EGCG was examined by Nanjo et al (Bioscience Biotechnology Biochemistry, 1999, 63(9):1621-1623) and found to be superior to other tea catechins in scavenging ROS such as superoxide anion and hydroxyl radicals—byproducts of hydrogen peroxide. Numerous studies have demonstrated that topically applied EGCG prevents these pathological changes and may help to prevent skin cancer. For example, experiments by Conney et al, (Proceedings National Academy Science USA 2002 99(19): 12455-60) have demonstrated significant reductions in both tumor incidence and size following topical EGCG application and UV radiation versus controls in mice specially bred for their susceptibility to cancer.

Katiyar et al (Clinical Cancer Research, 200 6:3864-3869) investigated the impact of pre-treating human skin with green tea polyphenols prior to exposure of varying doses of UVB (0.5, 1.0, 2.0, 4.0×MED). The results demonstrated significant inhibition of UVB-induced erythema responses at all UVB exposures. The same authors utilized skin biopsies from volunteer buttocks to study the effect of single applications of GTP (0.4, 0.8, 1.2 and 1.6 mg/$cm^2$ skin area) on UV-induced DNA damage in the form of cyclobutane pyrimidine dimers (CPD)—premutagenic lesions and the primary cause of melanoma. The results showed a significant dose-dependent decrease in CPD formation in both epidermis and dermis.

Of special interest are studies by Eun et al (The FASEB Journal, 2003 17(13):1913-article 10.1096/fj.02-0914fje. Published on line Aug. 1, 2003) that examined the effect of EGCG application under occlusion during a 6-week period to the buttocks of elderly healthy volunteers. Vehicle or EGCG-treated skin samples were obtained by punch biopsy. The EGCG application significantly stimulated the proliferation of structurally-supportive skin cells known as keratinocytes versus vehicle-treated samples along with a corresponding significant increase in epidermal thickness. In vitro experiments by the same authors demonstrated a dose-dependent stimulatory effect of EGCG on cultured keratinocytes and conversely, an inhibitory action against cultured squamous carcinoma cells, i.e., apoptosis. Of particular significance in these findings is the fact that two hallmarks of aging skin are both reduced skin thickness and keratinocyte cell growth and EGCG application has apparently reversed these trends. The anti-aging potential of EGCG was further demonstrated by these authors in a group of young volunteers. EGCG or vehicle control were applied to the buttocks during 48 hours and then treated with simulated solar radiation (2 MED). The protective action of EGCG against UV radiation was shown in skin biopsy results where a 4-fold greater increase in keratinocyte cell numbers were found in EGCG-treated samples versus vehicle-treated counterparts.

The inhibitory effect of EGCG on UVB-induced activation of nuclear factor kappa beta (NF-κB) in normal human epidermal keratinocytes (NHEK) was demonstrated by Mukhtar et al (Oncogene 2003 22:1035-440). NF-κB is a protein complex that is sequestered in the cytoplasm of almost all cell types by inhibitory protein kappa B (IκB) and is involved in cellular responses to stimuli such as stress, free radicals, ultraviolet irradiation and bacterial antigens. Once stimulated into action, NFκB sets off a cascade of proinflammatory cytokines such as tumor necrosis factor alpha (TNFα), interferon gamma (INF-γ), interleukin-1 and -8 (IL-1, IL-8) with implications in cancer, inflammatory diseases, septic shock, viral infection, and improper immune development. In the above-mentioned study the authors show that pretreatment of the keratinocytes to EGCG before UVB exposure resulted in a significant dose- and time-dependent inhibition of UVB-induced activation of NFκB. The results suggest that EGCG has the potential to protect against the adverse effects of UVB radiation via modulation in the NFκB pathway, thus protecting cellular targets against UVB-induced damage. The authors provide a molecular basis for the photo-chemopreventive effect of EGCG and suggest that green tea may be a useful agent against UVB-induced damage for human skin.

Epigallocatechin Gallate and Eczema

Eczema is a chronic inflammatory disease characterized by extreme itchiness, skin dryness, redness and inflammation initiated and exacerbated by stress and certain environmental factors such as extreme weather changes and allergens. Cutaneous infection, especially by *Staphylococcus aureus* and certain fungus such as *Trichophyton rubrum* and *Malassezia* spp, is known to be a contributing factor in eczema and often detected in the exzematous skin of patients. The antibacterial activity of whole and fractionated crude extracts of green tea (GTE) against various clinical isolates of pathogenic cutaneous bacteria was evaluated by Yam et al (FEMS Microbiology Letters 1997 152:169-74). The numbers of strains sensitive to GTE versus number strains tested were as follows: for *S. aureus* 33/33 (including 18 methicillin-resistant strains, MRSA), *S. epidermidis* (38/38) and *Corynebacterium* spp (2/2). The antibacterial activity of EGCG against 53 clinical isolates of MRSA was reported by Kono et al (The Journal of the Japanese Association of Infectious Diseases 1994 68(12):1518-22). The minimal inhibitory concentration (MIC) of EGCG was found to be 32-128 μg/ml against all strains. A time-kill study demonstrated that an isolate was bacteriostatic at 1-2 times the MIC and bactericidal at 6 times the MIC or ~0.04% aqueous solution against MRSA. The in vitro antifungal activity of EGCG against clinical isolates of various dermatophytes was reported by Park et al (Yonsei Medical Journal 2011 52(3):535-538). The authors demonstrated that among the dermatophyte species tested *T. rubrum* was the most susceptible to EGCG—more susceptible than to flucytosine and similar to fluconazole. The MIC value for 11 clinical isolates of this fungus ranged between 1-16 μg per mL.

Most *S. aureus* strains from atopic lesions produce enterotoxins with superantigen properties that are capable of inducing skin inflammation. Hisano et al (Archives of Dermatological Research 2003 295:183-189) used one such superantigen staphylococcal enterotoxin B (SEB) injected intraperitoneally, with or without EGCG, to monitor proinflammatory or cytokine inhibition in BALB/c mice. Serum levels for the two proinflammatory agents TNF-α and INF-γ were significantly reduced by EGCG versus control. Noh et al (International Immunopharmacology 2008 8:1172-1182) used a mite allergen extract (*Dermatophagoides pteronissinus*) applied topically to the ears of NC/Nga mice to induce atopic dermatitis (AD) type skin lesions. This inbred mice strain maintained in non air-controlled environments spontaneously suffer from AD-like skin lesions with markedly elevated serum levels of immunoglobulin E (IgE). Topical application of EGCG daily, following the allergen extract treatment, significantly reduced ear swelling and significantly lessened clinical signs provoked by the mite allergen extract such as erythema, edema, scaling and excoriation when compared to vehicle only application.

PRIOR ART

The patent literature describes various conventional topical formulations for green tea application. For example, Hernandez et al. (U.S. Pat. No. 7,314,634) provide claims using carbomer-based creams and serums to deliver green tea polyphenols to treat various skin conditions such as fine lines and wrinkles, acne rosacea, and other skin surface irregularities. McCook et al. (U.S. Pat. No. 5,306,486) describe oil-in-water and water-in-oil compositions containing green tea and various sunscreen agents. In prior animal studies using bioactive in organic solvent applications, Katiyar et al (Neoplasia 2003 5(6):555-65) recognized the need for a better topical delivery system and used a hydrophilic cream to demonstrate superior protection in a photocarcinogenetic study involving EGCG and a hairless mouse model. A more relevant patent application to this disclosure is that by Hara et al. (US Patent application 2010/0069476) who describe preferred topical hydrophilic formulations such as cream, mousse, lotion or spray for reducing photoageing comprising a catechin such as EGCG, or mixtures thereof, and an antioxidant ascorbic acid. Hydrophobic oily mixtures such as ointments and gels are also deemed suitable by these authors. The authors do suggest that the pH be adjusted to a neutral or slightly acid pH to match or approximate the pH of healthy skin yet use phosphate buffer (pH 7.0) in their exemplary hydrophilic cream.

Almost without exception these prior disclosures fail to recognize the importance of ascorbic acid inclusion and precise pH requirements in stabilizing phenolic-containing agents such as green tea catechins. These two factors, plus nitrogen blanketing during processing and packaging operations, were a major reason behind the stabilization of an oral liquid preparation containing EGCG and oligosaccharides in a now abandoned patent application by the present inventor (US 2009/0022852) and is also a major stability consideration in this disclosure. A minimal pH limit of 4.8 and appreciable overages needed to be established in order to assure product shelf life of 24 months at controlled room temperature conditions for both medicinal ingredients. A further disadvantage of conventional preparations is their limited skin bioactive permeation and localization properties.

Rationale for Liposomes as a Delivery System

Liposomes are generally referred to as multilamellar, oligolamellar or unilamellar vesicles and their potential as drug delivery systems for various applications have been well documented in the scientific literature during the past 30 years. The encapsulation of drugs into large multilamellar vesicles for topical application and their significantly enhanced skin penetration properties over conventional topical products was pioneered and patented (U.S. Pat. No. 4,761,288) by the late Dr. Michael Mezei at Dalhousie University in Halifax Nova Scotia. His method of preparation referred to as multiphase liposomal drug delivery system consisted of drug intercalated within lipid bilayers, drug dissolved in aqueous spaces both within the bilayers and the surrounding medium as well as drug present in a solid crystal or amorphous form. This method was an improvement of an earlier method originated by Bangham et al (Journal of Microbiology, 1965, 13:238-252).

Variations of these methods are widely used by scientists today and consist of dissolving drug and lipids (such as phospholipids, cholesterol, ceramides, etc) in organic solvents (e.g. chloroform, methanol, ether) within a round-bottom flask equipped with (or without) glass beads as a mixing contributor. Following removal of the solvent in a rotary evaporator under vacuum, an aqueous solution was than introduced into the flask and the contents gently agitated to release deposited film from flask walls, resulting in the formation of multilamellar vesicles. Unfortunately these methods are not conducive to scale-up or production possibilities.

Another widely-used method for achieving encapsulation efficiency for drugs involves a reverse-phase evaporation technique (Szoka F and Papahadjopoulos D, Proceedings of National Academy of Science USA, 1978, 75:4194-4198). Briefly, lipid components such as phospholipid and cholesterol are dissolved in a solvent or solvent mixture, e.g. methylene chloride—methanol, and a buffer solution containing water soluble drugs added to the solvent phase under brief sonication. The resulting emulsion is than roto-evaporated on a water bath to remove solvents. In a variation of this method, Williams et al (Journal of Pharmacy Pharmacology, 1991, 43:154-161) utilized alcohol in place of the pharmaceutically unacceptable solvents to prepare prolipo-some dispersions and thus eliminate the solvent evaporation step. Lipids, alcohol and Tris-HCl buffer (pH 7.4) were heated together at 60° C. to form proliposome mixtures which are than diluted to volume with the same Tris buffer under vortex-mixing to form liposome dispersions. The small proliposome batch sizes cited in the liposome preparation section (total 380 mg representing 3.8% of final volume) may pose scale-up problems when introduced into production. Also inattention to pH requirements plus lack of suitable anti-oxidant protection would have a deleterious effect on many of the polyphenols used as anti-inflammatory agents in the present disclosure.

Lipopharm and Unpublished Data:

In 1990 the present inventor cofounded a company Lipopharm Inc. to evaluate possible commercial scale-up possibilities for multilamellar vesicles based on the Mezei patents. Included in the agreement with Mezei were efforts to encapsulate two dermatological drugs—clobetasol propionate (CP) for the treatment of psoriasis and a titrated extract of Centella asiatica (TECA) for treating keloids and hypertrophic scars. The expectation was that reduced amounts of drug would be required and that liposomes would perform as effective penetration enhancers in delivering the drug into the deeper regions of the skin—especially clobetasol where the target site is the dermal vasculature for treating psoriasis.

A comparative skin drug distribution study involving application of Dermovate™ Cream (0.05% CP, Glaxo Canada) and two liposomal drug cream preparations (0.025 and 0.05% CP) were performed on the dorsal skins of hairless guinea pigs at the University of Montreal. A comparison of combined average drug concentrations in cutaneous tissues revealed no significant differences between the 0.025% liposomal clobetasol formulation and commercial product. Conversely total drug concentrations found in the cutaneous tissues with the 0.05% liposomal clobetasol formulation (705 ng) were more than double those found with Dermovate™ (338 ng). A pilot study involving the 0.025% liposomal TECA cream and psoriatic patients proved to be unsuccessful and was ultimately attributed to the phospholipid used in the liposomes.

The other drug investigated and very relevant to this disclosure was titrated extract of Centella asiatica (TECA) which had been commercially available for many years in both oral and conventional topical preparations for treatment of keloids and hypertrophic scars. A randomized, multi-centre, double-blind, placebo-controlled and parallel-design clinical study was arranged with several Canadian plastic surgeons and involved ~100 patients. The objective of the study was to determine the safety and efficacy of bi-daily application of 0.5% liposomed TECA cream versus a matching liposome placebo cream in accelerating the maturation of trauma, surgery or burn-induced hypertrophic scars and keloids. Patient visits were arranged at specified time intervals during a nine month period and in addition to scar measurement changes, clinical assessments at each scheduled visit consisted of rating on a scale of 0 to 5 for the following variables: inflammation, erythema, induration, pruritus and pain. The net result unfortunately demonstrated an unusually high placebo effect in which both treatments provided virtually identical efficacies with no statistical difference between treatments.

The rationale for the clinical results was ultimately attributed to an anti-inflammatory effect contributed by hydrogenated phosphatidylcholine (HPC), a major liposome component, whose effect unfortunately became public knowledge several years after the clinical trials were completed. HPC is obtained by hydrogenation of phosphatidyl choline (PC) where the unsaturated side chains of oleic and linoleic acids are converted to their saturated palmitic and stearic acid counterparts representing 16 and 18 carbon atoms respectively. This HPC effect was demonstrated in a study by Ghyczy and Vacata (Cosmetic Science and Technology: Skin Moisturization 2002 Volume 26 Chapter 15 pages 303-321) involving volunteers subjected to repeat arm washings with the skin irritant sodium lauryl sulfate (SLS). SLS challenge of human skin is generally recognized as the most convincing method for imitating dry skin conditions. The results demonstrated significant improvements in erythema associated with challenged skin samples treated with 1% aqueous HPC dispersion samples following the washings compared to those without HPC as determined by a Minolta Chromameter. The results also showed significant increases in skin moisture contents for the HPC dispersion. In a separate study involving healthy skin, addition of 2 and 4% HPC to conventional cream bases provided superior long acting hydration activity and smoothness features to the skin of healthy female volunteers when compared to similar conventional creams without HPC. The study involved twice daily cream applications during a 28 day time period and Corneometer readings taken at 28, 29 and 31 days. Both HPC formulations displayed similar efficacy with optimal beneficial effect apparently achieved at the 2% level. This latter observation may help to explain the lack of differences observed between active and placebo in the clinical trial cited above. Both liposomed TECA cream and its liposome placebo counterpart contained 2.5% and 1.5% HPC respectively and these increased concentrations are expected to contribute significant improvements to reddened and itchy dry skin conditions. The inclusion of HPC in the clobetasol formulations also explains the lack of clinical success in psoriasis patients since only low transition temperature phospholipids such as its unsaturated counterpart PC is capable of deeper penetration into the dermis (Bouwstra et al, Journal of Controlled Release 1998 56:189-96).

All liposomal formulations used in the aforementioned formulations and their methods of preparation and large scale production remained proprietary until now. The key element in the formulation is the preparation of a liposomal concentrate whereby bioactive ingredients and lipid components are pre-dissolved in alcohol rather than combined solvent-aqueous medium. Conventional cosmetic manufacturing equipment such as jacketed stainless steel containers and propeller stirrers were used throughout the entire processing operations. Such concentrates are then mixed with a predetermined cream base formulation. Ideally the base formulation (cream, lotion, etc) is oil-free but recognizing the fact that oil components may be necessary to serve as solubilizing agents when excess bioactives are not totally encapsulated, lack water solubility and thus present as undesirable crystals in the aqueous medium. This selective oil inclusion to avoid crystal/solute appearance in topical formulations differs from that of the Mezei multiphase system. Such oils were carefully selected for the base cream used in the liposomal TECA formulation to solubilize excess asiatic and madecassic acid components not encapsulated within the liposome bilayers. Highly unsaturated oil components should be minimized or excluded since exposure to ultraviolet radiation and oxygen can lead to generation of skin irritating peroxide-containing products.

The prime objective behind this disclosure therefore is to utilize the complementary anti-inflammatory properties of phospholipid-containing multilamellar vesicles for intradermal delivery and localization of phenolic anti-inflammatory agents to help prevent solar radiation-induced skin damage and to help prevent and/or treat skin inflammatory conditions resulting from eczema and other environmentally-induced skin adverse events.

There is also a need for topical compositions comprising phospholipid-containing multilamellar vesicles that are capable of delivering and localizing moisture into the upper skin layers.

A need also exists for topical compositions capable of reducing environmentally-induced reactive oxygen species and cyclobutane pyrimidine dimers in the skin.

There is a need also for topical compositions that may help to prevent photoageing by regenerating skin keratinocytes and thickening the stratum corneum.

There is also a long felt need for topical compositions that may help to prevent cancer and more particularly skin cancers such as squamous and basal cell carcinomas and melanomas.

The present invention generally fulfils at least some of these needs and also other needs which will be apparent to those skilled in the art upon reading the following specification.

SUMMARY OF THE INVENTION

According to an aspect of the present invention, it is provided a topical composition comprising lipid-containing lamellar bilayer vesicles and at least one phenolic anti-inflammatory agent.

According to one aspect of the invention, it is provided a method for preparing an aqueous liposome concentrate composition, the concentrate composition being adapted for being dispersed into a cosmetically-acceptable base, said method comprising the steps of:
 a) mixing and dissolving into one or more cosmetically-acceptable alcohols:
  one or more phenolic anti-inflammatory agents,
  one or more glycerophospholipids, and
  one or more skin-related lipids selected from the group consisting of cholesterol, cholesterol derivatives, ceramides, sphingomyelin, long chain fatty acids and mixtures thereof;
 step a) being performed at a temperature superior to the transition temperature of the glycerophospholipid and under nitrogen blanketing;
 b) adding an aqueous medium to the solution made in a) with constant stirring until formation of the liposome concentrate composition as a homogeneous milky dispersion; step b) being performed at a similar temperature than in step a) and under nitrogen blanketing;

According to one aspect of the invention, the liposome concentrate composition comprises spherical vesicles having membranes in a bilayer arrangement of said one or more phenolic anti-inflammatory agents, said one or more glycerophospholipids and said one or more skin-related lipids.

According to one aspect of the invention, it is provided a topical composition comprising an aqueous liposome concentrate composition as prepared by the method disclosed herein, and dispersed under nitrogen blanketing in a cosmetically-acceptable aqueous base having an acidic pH and optionally comprising an antioxidant.

According to one aspect of the invention, it is provided a method for reducing inflammatory skin conditions comprising the step of administering an effective amount of the topical composition disclosed herein to a subject in need thereof. Preferably, the inflammatory skin conditions are redness, itchiness or dryness of the skin due to atopic dermatitis, allergic dermatitis, contact dermatitis, or environmentally-induced skin damage.

According to another aspect of the invention, there is provided a method to help prevent solar radiation-induced skin damage comprising administering a topical composition as defined hereinbefore to a human.

According to one more aspect, there is provided a method to help prevent and/or prevent red itchy dry skin conditions due to eczema and contact dermatitis by comprising administering a topical composition as defined hereinbefore to a human.

According to yet another aspect, there is provided a method to increase skin hydration by comprising administering a topical composition as defined hereinbefore to a human.

According to a further related aspect, there is provided a method to reduce solar radiation-induced reactive oxygen species and cyclobutane pyrimidine dimers in the skin.

According to yet one other aspect of the invention, there is provided a method to help prevent ageing by regenerating skin keratinocytes.

According to another related aspect, the invention relates to the use of a topical composition with a liposome-encapsulated phenolic anti-inflammatory agent for inhibiting growth of squamous carcinoma cells and helping to generally prevent skin cancer.

The present invention fulfils these needs and also other needs which will be apparent to those skilled in the art upon reading the following specification.

DETAILED DESCRIPTION OF THE PREFERRED EMBODIMENTS

According to a preferred aspect of the invention, it is provided topical compositions containing lamellar bilayer vesicles comprised of glycerophospholipids, stratum corneum type lipids and one or more encapsulated phenolic anti-inflammatory agents.

Preferably the bilayer vesicles are unilamellar, oligolamellar or multilamellar, more preferably multilamellar vesicles.

Preferably the vesicles are comprised of glycerophospholipids from natural or synthetic sources. Preferably the natural glycerophospholipids are chosen from egg or soy lecithin, and more preferably from soy lecithin. Preferably the glycerophospholipids are chosen from one or more of phosphatidylcholine, phosphatidylglycerol, phosphatidylserine, phosphatidylinositol, phosphatidic acid, phosphatidylethanolamine. More preferably the glycerophospholipid is chosen from phosphatidylcholine, and more preferably a phosphatidylcholine with side chains comprised of 10 to 18 carbon atoms and even more preferably with saturated side chains. Preferably the glycerophospholipids are present in the final topical composition at a concentration of about 1% to about 4%, and more preferably between 1.5 and 2.5%.

Preferably the stratum corneum type lipids are present in the final topical composition at a concentration of about 0.001% to about 0.10%. Preferably, the stratum corneum lipids are chosen from cholesterol and its derivatives, ceramides, sphingomyelin, long chain fatty acids such as stearic, palmitic and myristic acid.

Preferably the phenolic anti-inflammatory agent is present in the composition at a concentration of about 0.1% to about 5%, more preferably 0.5 to 2.5% (all weights given herein are by percentages unless otherwise specified). Preferably, the phenolic anti-inflammatory agent is chosen from natural or synthetic sources. More preferably the phenolic agent is selected from plant, fruit, and vegetable sources such as a green tea catechin, proanthocyanidins, resveratrol, curcumin, silibinin, silymarin, carnosic acid, genestein, nordihydroguaiaretic acid, apigenin, quercetin, caffeic acid, ferulic acid, kaempferol. Preferably, the anti-inflammatory agent is selected from green tea catechins, and even more preferably epigallocatechin gallate.

The final compositions of the invention may further include from about 0.5 to 3% ethyl alcohol; from about 1% to about 10% of a humectant; from about 1% to about 5% of an emollient; from about 1% to about 5% of a viscosity promoting agent; from about 0.1% to about 2% of an alkalizing agent; from about 0.05 to about 0.25% of an antioxidant; from about 0.1% to about 2% of a preservative.

Preferably, the humectant is selected from glycerol, propylene glycol and sorbitol.

Preferably, the emollient is selected from a vegetable oil, mineral oil or a fatty acid ester, or mixtures thereof that are capable of providing a solubility support role for poorly water soluble and non-encapsulated polyphenols presenting with crystal deposition in the continuous aqueous phase.

Preferably, the viscosity-promoting agent is selected from polyvinyl carboxy polymers, polyacrylamides, guar gum, xanthan gum, *caesalpinia spinosa* gum, alginates, carboxymethylcelluose (CMC), hydroxyethyl cellulose (HEC), gum arabic, locust bean gum, tragacanth, agar agar, or mixtures thereof. More preferably, the viscosity-promoting agent consists of polyacrylamides and *caesalpinia spinosa* gum.

Preferably, the alkalizing agent is selected from citrates, phosphates, acetates, ascorbates, and triethanolamine. More preferably, it consists of triethanolamine.

Preferably the pH is adjusted in the range of 4.0 to 4.8, more preferably in the range of 4.4 to 4.6.

Preferably the antioxidant is selected from ascorbic acid, its esters or its sodium salt, or mixtures thereof.

Preferably, the preservative is selected from methylparaben, propylparaben, butylparaben, phenoxyethanol, benzoic acid, diazolidinyl urea, sorbic acid or its salts, or mixtures thereof. More preferably, the preservative is a mixture of methylparaben, propylparaben and diazolidinyl urea.

1) Processes for Preparing Liposome Concentrate Compositions

According to another aspect of the invention there is provided processes for preparing liposome concentrate compositions that are easily dispersed into conventional topical hydrophilic base compositions. Although any method and material similar to those described herein can be used in the practice for testing of the present invention, the preferred methods and materials are described.

According to a preferred aspect of the invention the entire processing operation is conducted under nitrogen blanketing.

The batch sizes for the liposome concentrate phase of the operation are preferably in the range of about 5 to 40% of the final topical composition, more preferably in the range of about 15 to about 25% percent.

Alcohol, glycerophospholipid, other stratum corneum type lipids and one or more phenolic anti-inflammatory agents are stirred until dissolved in a suitable container. In a separate container purified water is added in small portions to the alcohol phase with continuous stirring. When transition temperatures (TC) of the glycerophospholipids exceed room temperatures, both alcohol and aqueous phases are preheated to temperatures several degrees above TC. The water phase is initially added slowly and immediately following a thickening and then thinning phase of the stirred dispersion, the water phase can be added at a more rapid rate. In the event of excessive precipitation problems occurring during the concentrate preparation, a suitable portion of the contributing bioactive agent(s) must be removed from the batch and incorporated in the base cream phase with special attention to its oil/water solubility characteristics and inclusion if necessary of appropriate oil-solubilizing ingredients. The end result for the liposome concentrate composition is a homogeneous milky emulsion which is stored under nitrogen blanketing in well-sealed containers until required.

The base composition is easily prepared by anyone skilled in the art. The liposome concentrate is than added to the base composition with continuous stirring and storage under nitrogen until required for packaging.

EXAMPLES

The following example is illustrative of the wide range of applicability of the present invention and is not intended to limit its scope. Modifications and variations can be made therein without departing from scope of the invention. Although any method and material similar or equivalent to those described herein can be used in the practice for testing of the present invention, the preferred methods and materials are described.

Example 1

Gel-Cream:

In this formulation containing 0.5% EGCG, it was necessary to reduce the bioactive to approximately 40% in the concentrate component because of excessive precipitation occurring when the total amount of EGCG was used in the preparation. Bioactive remainder possessing adequate water solubility properties is easily included in the base cream aqueous phase. Since the transition temperature of hydrogenated phosphatidylcholine is ~55° C., both alcohol and aqueous phases in the concentrate portion need to be preheated to ~58-62° C. prior to mixing.

Part 1—15% Concentrate:

| Ingredients | % in Conc. | % in Cream |
|---|---|---|
| *Phospholipon 90H ™ | 11.000 | 2.200 |
| **Teavigo ™ | 0.950 | 0.190 |
| Ceramide 2 | 0.015 | 0.003 |
| Cholesterol | 0.060 | 0.012 |
| Alcohol | 10.000 | 2.000 |
| Purified Water | 52.950 | 10.595 |
| TOTAL | 100.000 | 15.000 |

*Hydrogenated soy phosphatidylcholine (HPC), Lipoid LLC, Newark NJ;
**Epigallocatechin gallate, DSM Nutrition;

Part 2—85% Cream Base:

| Ingredients | % |
|---|---|
| Purified Water | 73.790 |
| Ascorbic acid | 0.200 |
| Teavigo | 0.310 |
| Sorbitol 70% | 4.000 |
| Triethanolamine (50%) - QS to adjust pH to 4.5 ± 0.1 | 0.260 |
| Isopropyl Palmitate | 2.500 |
| Cyclomethicone | 1.000 |
| Germaben II | 1.000 |
| Sepigel 307 | 1.100 |
| Solagum Tara | 1.100 |
| TOTAL | 85.000 |

Part 3—Final Formulation Processing:

Add Part 1 to Part 2 with continuous stirring under nitrogen blanketing. Final pH=4.50.

Example 2

Antibiotic-Induced Skin Rashes:

The formulation provided in EXAMPLE 1 was used to treat severe skin rashes developed on the legs and arms of an 82 year old woman who had been prescribed the antibiotic Cipro by her physician to treat a lung infection. The itching was severe enough to cause spot bleeding at some skin sites due to scratching but most importantly to her discomfort was lack of sleep at night. Cream application not only immediately relieved the itching but allowed her to sleep uninterrupted through the first and subsequent nights after applying the medication. Cipro administration was eventually stopped due to occurrence of another more serious adverse event but her affected skin areas had returned to normal.

Example 3

Mild-to-Moderate Eczema:

The formulation provided in EXAMPLE 1 was used in a short term study to treat a 48 year old woman who has had eczema year-round all her life and is currently employed in the international marketing department of a pharmaceutical company. She previously used OTC hydrocortisone creams to relieve itching on her hands and other skin areas during eczema flare-up episodes. Her experience with our formulation as recorded in a daily diary started with eczema flare-ups caused by onset of cold wintry weather and use of heavy clothing. The flare-ups included dry itchy cracked skin on hands as well as itching and redness in the neck area brought on through skin contact with a scarf or wool coat. Twice daily cream application, morning after showering and evening before retirement, was performed over a 4 day period. After Day 1 she recorded less itching and the cream to be instantly soothing and Day 2 starting to see the eczema diminish. After Day 3 she observed "remarkable improvement" with no evidence of itchiness and redness is gone. After Day 4 her hands had almost healed but skin still a little raw. However symptoms of eczema had disappeared and the neck area had completely healed. Her overall comment on the cream was that the formulation was soothing and moisturized the skin immediately.

Example 4

Severe Eczema:

The formulation provided in EXAMPLE 1 was used on nightly application only along with Betaderm (betamethasone valerate) by a 52 year old woman who has had a more severe form of eczema year-round all her life and is currently employed in the nursing profession. Her eczema consisted of redness, scaling and swelling appearing on crack on little finger along with lesions behind the right knee and inside the right elbow. Her overall comments of the cream after a four day application were that once the eczema episode is gone the cream seems to keep the eczema away. Her personal feeling of the cream is very good to keep the eczema away and a great moisturizer but does not appear to heal the lesions.

INCORPORATION BY REFERENCE

The entire contents of all published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. The contents of all references, issued patents, and published patent applications cited throughout this application are hereby incorporated by reference.

What is claimed is:

1. A method for preparing an aqueous liposome concentrate composition to be dispersed into a cosmetically-acceptable base, said method comprising the steps of:
   a) mixing and dissolving into one or more cosmetically-acceptable alcohol solvents:
      one or more phenolic anti-inflammatory agents,
      one or more glycerophospholipids, and
      one or more skin-related lipids selected from the group consisting of cholesterol, cholesterol derivatives, ceramides, sphingomyelin, long chain fatty acids and mixtures thereof;
      step a) being performed at a temperature superior to the transition temperature of the glycerophospholipid and under nitrogen blanketing; and
   b) adding an aqueous medium to the solution made in a) with constant stirring until formation of the liposome concentrate composition as a homogeneous milky dispersion;
      step b) being performed at a similar temperature than in step a) and under nitrogen blanketing.

2. The method as claimed in claim 1 wherein the liposome concentrate composition comprises spherical vesicles having membranes in a bilayer arrangement of said one or more phenolic anti-inflammatory agents, said one or more glycerophospholipids and said one or more skin-related lipids.

3. The method as claimed in claim 1, wherein the one or more phenolic anti-inflammatory agents comprise green tea catechin, proanthocyanidin, resveratrol, curcumin, silibinin, silymarin, carnosic acid, genestein, nordihydroguaiaretic acid, apigenin, quercetin, caffeic acid, ferulic acid, ellagic acid, kaempferol or a mixture thereof.

4. The method as claimed in claim 1, wherein the phenolic anti-inflammatory agent is epigallocatechin gallate.

5. The method as claimed in claim 1, wherein the one or more glycerophospholipids are phosphatidylcholine, phosphatidylglycerol, phosphatidylethanolamine, phosphatidylserine, phosphatidic acid, phosphatidylinositol or a mixture thereof.

6. The method as claimed in claim 1, wherein the one or more cosmetically acceptable alcohol solvents is ethyl alcohol.

7. The method as claimed in claim 2, wherein the spherical vesicles comprise multilamellar membranes.

8. A topical composition comprising an aqueous liposome concentrate composition as prepared by the method of claim 1, and dispersed under nitrogen blanketing in a cosmetically-acceptable aqueous base having an acidic pH and optionally comprising an antioxidant.

9. The topical composition as claimed in claim 8, wherein the liposome concentrate composition contains epigallocatechin gallate and further comprises a water soluble antioxidant selected from ascorbic acid and its derivatives.

10. The topical composition as claimed in claim 9, having a pH value between 4.2 and 4.6.

11. The topical composition of claim 8, wherein the liposomal composition is present at a concentration of 5% to 40% by weight of the topical composition.

12. The topical composition of claim 8, wherein the topically acceptable base is in a form of a suspension, a gel, a cream or a lotion.

13. The topical composition as claimed in claim 8, wherein the one or more phenolic anti-inflammatory agents comprise green tea catechin, proanthocyanidin, resveratrol, curcumin, silibinin, silymarin, carnosic acid, genestein, nordihydroguaiaretic acid, apigenin, quercetin, caffeic acid, ferulic acid, ellagic acid, kaempferol or a mixture thereof.

14. The topical composition as claimed in claim 8, wherein the phenolic anti-inflammatory agent is epigallocatechin gallate.

15. The topical composition as claimed in claim 8, wherein the one or more phenolic anti-inflammatory agents are present at a concentration of about 0.1% to about 5.0%.

16. The topical composition as claimed in claim 8, wherein the one or more glycerophospholipids are phosphatidylcholine, phosphatidylglycerol, phosphatidylethanolamine, phosphatidylserine, phosphatidic acid, phosphatidylinositol or a mixture thereof.

17. The topical composition as claimed in claim 16, wherein the one or more glycerophospholipids are present at a concentration of about 1% to about 4%.

18. The topical composition as claimed in claim 8, wherein the one or more skin-related lipids are present at a concentration of about 0.001% to about 0.1%.

19. The topical composition as claimed in claim 8, wherein the cosmetically-acceptable alcohol solvent is ethyl alcohol.

20. The topical composition as claimed in claim 19, wherein the ethyl alcohol is present at a concentration of about 0.5% to about 3%.

21. A method for reducing inflammatory skin conditions comprising the step of administering an effective amount of the topical composition as claimed in claim 8 to a subject in need thereof.

22. The method as claimed in claim 21, wherein the inflammatory skin conditions are redness, itchiness or dryness of the skin due to atopic dermatitis, allergic dermatitis, contact dermatitis, or environmentally-induced skin damage.

* * * * *